United States Patent
Harrington et al.

(10) Patent No.: US 9,573,889 B2
(45) Date of Patent: Feb. 21, 2017

(54) METHODS AND COMPOSITIONS FOR MAKING AN AMINO ACID TRIISOCYANATE

(71) Applicant: Warsaw Orthopedic, Inc., Warsaw, IN (US)

(72) Inventors: Roger E. Harrington, Collierville, TN (US); Kerem N. Kalpakci, Memphis, TN (US); David S. Scher, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/048,541

(22) Filed: Feb. 19, 2016

(65) Prior Publication Data

US 2016/0168085 A1 Jun. 16, 2016

Related U.S. Application Data

(62) Division of application No. 14/153,419, filed on Jan. 13, 2014, now Pat. No. 9,266,824.

(51) Int. Cl.
| | | |
|---|---|---|
| *C07C 265/14* | (2006.01) |
| *C07C 263/10* | (2006.01) |
| *C07C 263/20* | (2006.01) |
| *C01B 31/28* | (2006.01) |
| *C08G 18/00* | (2006.01) |
| *C08G 18/77* | (2006.01) |
| *C08G 18/32* | (2006.01) |

(52) U.S. Cl.
CPC ............. *C07C 265/14* (2013.01); *C01B 31/28* (2013.01); *C07C 263/10* (2013.01); *C07C 263/20* (2013.01); *C08G 18/00* (2013.01); *C08G 18/3206* (2013.01); *C08G 18/771* (2013.01)

(58) Field of Classification Search
None
See application file for complete search history.

(56) References Cited

U.S. PATENT DOCUMENTS

| | | | |
|---|---|---|---|
| 2,542,449 A | 5/1953 | Morningstar et al. |
| 3,544,611 A | 12/1970 | Michelet et al. |
| 4,278,809 A | 7/1981 | Burdett |

(Continued)

FOREIGN PATENT DOCUMENTS

| | | |
|---|---|---|
| EP | 2275150 A2 | 1/2011 |
| EP | 2275150 A3 | 4/2013 |

(Continued)

OTHER PUBLICATIONS

Machine Translaton of RU 2299852 2007.*

*Primary Examiner* — Karl J Puttlitz

(57) ABSTRACT

A method of making an amino acid triisocyanate is provided, the method comprising reacting an amino acid trihydrochloride with phosgene to form the amino acid triisocyanate. In some embodiments, the amino acid trihydrochloride comprises lysine ester trihydrochloride salt and the amino acid triisocyanate comprises lysine ester triisocyanate. In some embodiments, there is a lysine ester triisocyanate having a purity of at least about 98%, the lysine ester triisocyanate having a structure resulting from reacting lysine ester trihydrochloride salt with phosgene to form the lysine ester triisocyanate. These lysine ester triisocyanates can be used to make biodegradable polyurethanes.

4 Claims, 4 Drawing Sheets

(56) References Cited

U.S. PATENT DOCUMENTS

| | | |
|---|---|---|
| 4,422,976 A | 12/1983 | Yamamoto et al. |
| 5,136,086 A | 8/1992 | Nagata et al. |
| 5,523,467 A | 6/1996 | Okazaki et al. |
| 5,633,396 A | 5/1997 | Bischof et al. |
| 6,399,822 B1 * | 6/2002 | Eckert .................. B01J 7/00 562/847 |
| 6,416,686 B2 | 7/2002 | Bruchmann et al. |
| 7,112,694 B2 | 9/2006 | Woelfert et al. |
| 7,339,020 B2 | 3/2008 | Bruchmann et al. |
| 7,482,481 B2 | 1/2009 | Rohde et al. |
| 7,897,806 B2 | 3/2011 | Sesing et al. |
| 8,097,751 B2 | 1/2012 | Koch et al. |
| 2006/0051394 A1 | 3/2006 | Moore et al. |
| 2006/0167303 A1 | 7/2006 | Yamasaki et al. ............. 560/1 |
| 2007/0275033 A9 | 11/2007 | Moore et al. |
| 2008/0262613 A1 | 10/2008 | Gogolewski |
| 2009/0081270 A9 | 3/2009 | Moore et al. |
| 2009/0124785 A1 | 5/2009 | Shimakawa et al. |
| 2009/0130174 A1 | 5/2009 | Guelcher et al. |
| 2009/0142506 A1 | 6/2009 | Roesler et al. |
| 2009/0209784 A1 | 8/2009 | Lorenz et al. |
| 2011/0015672 A1 | 1/2011 | Stopek |
| 2011/0105785 A1 | 5/2011 | Knoesche et al. |
| 2011/0213177 A1 | 9/2011 | Mattke et al. |
| 2011/0275854 A1 | 11/2011 | Daussin et al. |
| 2011/0306786 A1 | 12/2011 | Perret et al. |
| 2012/0004446 A1 | 1/2012 | Mattke et al. |
| 2012/0016154 A1 | 1/2012 | Mattke et al. |
| 2012/0095255 A1 | 4/2012 | Mattke et al. |
| 2012/0202961 A1 | 8/2012 | Bhattacharyya et al. ...... 528/85 |
| 2013/0023694 A1 | 1/2013 | Steiger et al. |
| 2013/0060062 A1 | 3/2013 | Mattke et al. |

FOREIGN PATENT DOCUMENTS

| | | |
|---|---|---|
| JP | 53135931 | 11/1978 |
| WO | 9617881 A1 | 6/1996 |
| WO | 9825888 A1 | 6/1998 |
| WO | 2005089778 A1 | 9/2005 |
| WO | 2006010278 A1 | 2/2006 |
| WO | 2010021335 A1 | 2/2010 |
| WO | 2011104264 A1 | 9/2011 |
| WO | 2012027162 A2 | 3/2012 |
| WO | 2012027162 A3 | 3/2012 |
| WO | 2012049158 A1 | 4/2012 |
| WO | 2012106588 A2 | 8/2012 |
| WO | 2012106588 A3 | 8/2012 |
| WO | 2013029918 A1 | 7/2013 |

* cited by examiner

METHODS AND COMPOSITIONS FOR MAKING AN AMINO ACID TRIISOCYANATE

This application is a divisional application of U.S. patent application Ser. No. 14/153,419 filed Jan. 13, 2014, entitled "METHODS AND COMPOSITIONS FOR MAKING AN AMINO ACID TRIISOCYANATE". This entire disclosure is incorporated herein by reference into the present disclosure.

BACKGROUND

Isocyanate is a functional group having the formula R—N=C=O. A molecule which contains more than one isocyanate groups is referred to as a polyisocyanate (diisocyanate, triisocyanate, etc.). Isocyanates are generally highly reactive.

Isocyanates are capable of forming polyurethanes or polyureas when reacted with molecules containing one or more hydroxyl functional groups (e.g., alcohol, polyols, etc.) or amino functionality (—$NH_2$) such as in polyamines to form polyureas. A typical reaction resulting in the formation of a polyisocyanate with an alcohol to form a polyurethane is shown below:

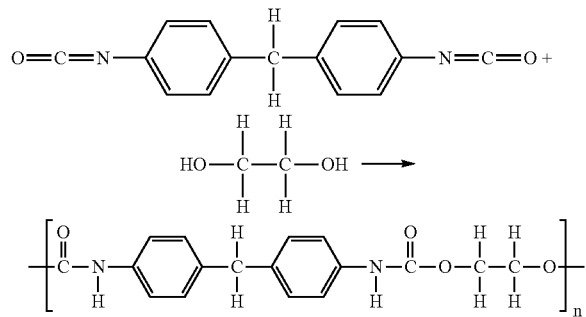

Polyurethanes can be used as implantable material either as implants either preformed and then implanted into the target tissue site or as a flowable material that is implanted at the site, where the polyurethane adheres and/or hardens at the target tissue site (e.g., tissue defect, bone defect, etc.). In some embodiments, the polyurethane is porous and allows cells into the site to aid in remodeling and repair of the defect, where it can then degrade over time (e.g., 2 weeks to 6 months or longer).

To make polyisocyanates, phosgene (COCl2) can be used. Phosgene is a valued industrial reagent and building block in the synthesis of pharmaceuticals and other organic compounds. However, phosgene is toxic and great care should be used in its handling.

There is a need for new methods and compositions to efficiently and safely make polyisocyanates. Methods and compositions that can efficiently and safely generate phosgene are also needed.

SUMMARY

New compositions and methods are provided to efficiently and safely make polyisocyanates including lysine ester triisocyanate. Methods and compositions that can efficiently and safely generate phosgene are also provided.

In one embodiment, there is a method of making an amino acid triisocyanate, the method comprising reacting an amino acid trihydrochloride with phosgene to form the amino acid triisocyanate. In some embodiments, the polyisocyanate comprises lysine ester triisocyanate. Additionally, in some embodiments, the method takes place in a single reaction vessel.

In another embodiment, there is a method of making phosgene, the method comprising heating triphosgene to form phosgene and recovering phosgene in an aromatic liquid containing chlorine.

In some embodiments, there is a method for making a polyisocyanate by decomposing triphosgene using heat in the presence of a catalyst to form phosgene, which can then be used to make the polyisocyanate. In some embodiments, the catalyst comprises cobalt phthalocyanine or 1,10-phenanthroline. In some embodiments, the phosgene is recovered in liquid chlorobenzene or dichlorobenzene.

In some embodiments, there is a lysine ester triisocyanate having a purity of at least about 98%, the lysine ester triisocyanate having a structure resulting from reacting lysine ester trihydrochloride salt with phosgene to form the lysine ester triisocyanate.

In some embodiments, there is a method of making a polyurethane or polyuria comprising reacting a lysine ester triisocyanate with one or more of a polyol or a polyamine (to form a polyurea). The polyamine reacted with the lysine ester triisocyanate will form the polyurea. The polyurethane or polyurea may be biodegradable or biocompatible.

In some embodiments, there is a method of making an amino acid trihydrochloride, the method comprising reacting an amino acid monohydrochloride with an alkanolamine to form the amino acid trihydrochloride. The amino acid monohydrochloride can comprise lysine HCl and the alkanolamine can comprise ethanolamine and the amino acid trihydrochloride can comprise lysine ester trihydrochloride.

In some embodiments, there is a method of making a lysine ester trihydrochloride salt, the method comprising reacting lysine hydrochloride and ethanolamine to form the lysine ester trihydrochloride salt.

In some embodiments, there is a lysine ester trihydrochloride salt having a purity of at least about 95% or at least about 98%, the lysine ester trihydrochloride salt having a structure resulting from reacting lysine hydrochloride and ethanolamine to form the lysine ester trihydrochloride salt. In some embodiments, the lysine ester trihydrochloride salt is isolated in crystalized form and dissolved in methanol and/or ethanol to form a lysine ester trihydrochloride and methanol and/or ethanol mixture and the lysine ester trihydrochloride is removed from the mixture to form a high purity recrystallized lysine ester trihydrochloride having a purity of from about 99% to about 99.99%. Therefore, the lysine ester trihydrochloride can have a high purity.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION

Figure 1:
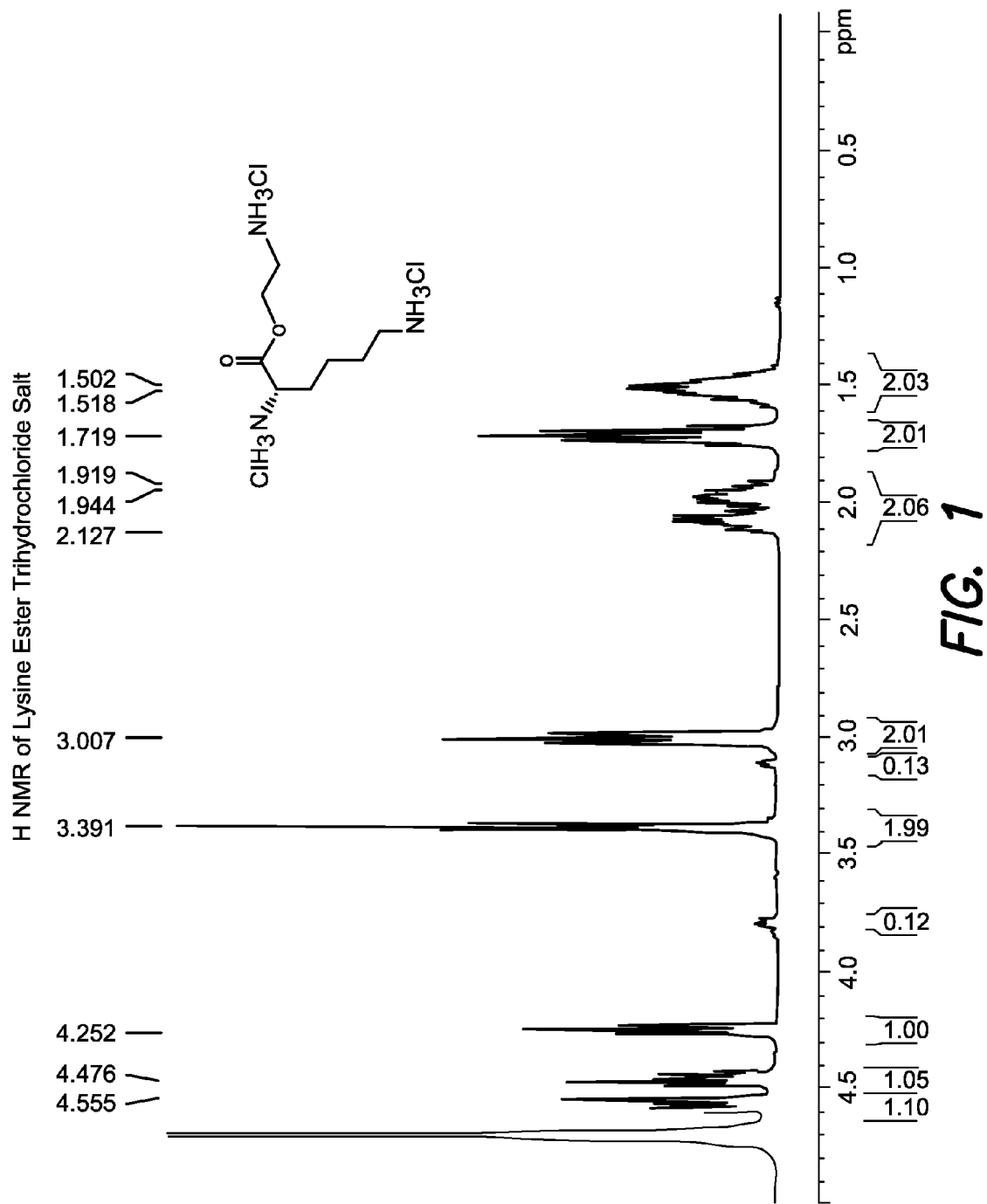
FIG. 1 is a graphic illustration of the $^1$H NMR data obtained from isolated and purified lysine ester trihydrochloride salt.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an alkanolamine" includes one, two, three or more alkanolamines.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug".

The term "biodegradable" includes all or parts of the matrix that will degrade over time by the action of enzymes, by hydrolytic action and/or by other similar mechanisms in the human body. In various embodiments, "biodegradable" includes that the matrix can break down or degrade within the body to non-toxic components as cells (e.g., bone cells) infiltrate the matrix and allow repair of the defect. By "bioerodible" it is meant that the matrix will erode or degrade over time due, at least in part, to contact with substances found in the surrounding tissue, fluids or by cellular action. By "bioabsorbable" it is meant that the matrix will be broken down and absorbed within the human body, for example, by a cell or tissue. "Biocompatible" means that the matrix will not cause substantial tissue irritation or necrosis at the target tissue site and/or will not be carcinogenic.

The term "polyurethane" and "PUR" as used herein, is intended to include all polymers incorporating more than one urethane group (—NH—CO—O—) in the polymer backbone. Polyurethane materials, in some embodiments, refer to the compositions formed by the reaction of a polyisocyanate (such as a triisocyanate) and a polyol (such as a diol) or polyamine, optionally with any additional components. In some embodiments, the polyamine can react with the polyisocyanate to form a polyurea. Typical reaction to form a polyurethane is shown below, where R1 and R2 are alkyl moieties:

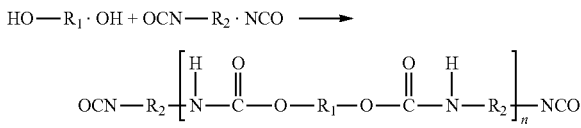

The term "polyisocyanate," as that term is used herein, encompasses any chemical structure comprising two or more isocyanate groups. A "diisocyanate," as used herein, is a subset of the class of polyisocyanates, a chemical structure containing two isocyanate (—OCN) groups. A "triisocyanate," as used herein, is a subset of the class of polyisocyanates, a chemical structure containing three isocyanate (—OCN) groups. Similarly, a "polyol" contains two or more alcohol (—OH) groups, while a "diol" contains two alcohol groups, and a "polyamine" contains two or more amine groups (e.g., primary amine groups).

The polyurethane or polyurea can contain growth factors. As used herein, "growth factors" are chemicals that regulate cellular metabolic processes, including but not limited to differentiation, proliferation, synthesis of various cellular products, and other metabolic activities. Growth factors may include several families of chemicals, including but not limited to cytokines, eicosanoids, and differentiation factors, such as, for example, platelet-derived growth factor (PDGF). Other factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein. Other growth factors include GDF-5, the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenic proteins including all BMPs, including but not limited to BMP-2, BMP-4, and BMP-7.

The polyurethane or polyurea can be "osteogenic," where it can enhance or accelerate the ingrowth of new bone tissue by one or more mechanisms such as osteogenesis, osteoconduction and/or osteoinduction.

In some embodiments, polyurethane materials refer to the compositions formed from the reaction of a polyisocyanate (such as a triisocyanate) and a polyol (such as a diol), and optionally a catalyst.

New compositions and methods are provided to efficiently and safely make polyisocyanates including lysine ester triisocyanate. Methods and compositions that can efficiently and safely generate phosgene are also provided.

In one embodiment, there is a method of making an amino acid triisocyanate, the method comprising reacting an amino acid trihydrochloride with phosgene to form the amino acid triisocyanate. In some embodiments, the polyisocyanate comprises lysine ester triisocyanate. Additionally, in some embodiments, the method takes place in a single reaction vessel.

In another embodiment, there is a method of making phosgene, the method comprising heating triphosgene to form phosgene and recovering phosgene in an aromatic liquid containing chlorine.

In some embodiments, there is a method for making a polyisocyanate by decomposing triphosgene using heat in the presence of a catalyst to form phosgene, which can then be used to make the polyisocyanate. In some embodiments, the catalyst comprises cobalt phthalocyanine or 1,10-phenanthroline. In some embodiments, the phosgene is recovered in liquid chlorobenzene or dichlorobenzene.

In some embodiments, there is a lysine ester triisocyanate having a purity of at least about 98%, the lysine ester triisocyanate having a structure resulting from reacting lysine ester trihydrochloride salt with phosgene to form the lysine ester triisocyanate.

In some embodiments, there is a method of making an amino acid trihydrochloride, the method comprising reacting an amino acid monohydrochloride with an alkanolamine to form the amino acid trihydrochloride. In some embodiments, the amino acid monohydrochloride comprises lysine HCl and the alkanolamine comprises ethanolamine and the amino acid trihydrochloride comprises lysine ester trihydrochloride.

In some embodiments, there is a method of making a lysine ester trihydrochloride salt, the method comprising reacting lysine hydrochloride and ethanolamine to form the lysine ester trihydrochloride salt.

In some embodiments, there is a lysine ester trihydrochloride salt having a purity of at least about 95% or at least about 98%, the lysine ester trihydrochloride salt having a structure resulting from reacting lysine hydrochloride and ethanolamine to form the lysine ester trihydrochloride salt.

The section headings below should not be restricted and can be interchanged with other section headings.

Amino Acid Salts

The compositions and methods of making amino acid polyisocyanates include making an amino acid salt and using this salt to produce the amino acid polyisocyanate. Amino acid salts useful to make the amino acid polyisocyanates include salts of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or a combination thereof. Exemplary polyisocyanates for use in embodiments of the present application include but are not limited to 2,6-triisocyanato methyl caproate, arginine triisocyanate, asparagine triisocyanate, proline triisocyanate, glutamine triisocyanate, lysine triisocyanate, lysine ethyl ester triisocyanate, lysine methyl ester triisocyanate, lysine propyl ester triisocyanate, or derivatives thereof. In some embodiments, the polyisocyanate is biocompatible, biodegradable, and/or bioresorbable.

Some salt forms of the amino acid that can be used in the present application include those salt-forming acids and bases that do not substantially increase the toxicity of a compound, such as, salts of alkali metals such as magnesium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycolic, gluconic, gulonic, succinic, arylsulfonic, e.g., p-toluenesulfonic acids, and the like.

In some embodiments, the amino acid salt can be in monohydrochloride, dihydrochloride or trihydrochloride form. In some embodiments, the amino acid salt comprises lysine HCl. In some embodiments, the amino acid monohydrochloride salt comprises at least one of arginine HCl, histidine HCl, lysine HCl, aspartic acid HCl, glutamic acid HCl, serine HCl, threonine HCl, asparagine HCl, glutamine HCl, cysteine HCl, selenocystein HCl, glycine HCl, proline HCl, alanine HCl, valine HCl, isoleucine HCl, leucine HCl, methionine HCl, phenylalanine HCl, tyrosine HCl, or tryptophan HCl.

The amino acid salt is reacted with an alkanolamine to produce the amino acid trihydrochloride salt. Suitable amino acid trihydrochloride salts include, for example, lysine trihydrochloride, arginine trihydrochloride, histidine trihydrochloride, lysine trihydrochloride, aspartic acid trihydrochloride, glutamic acid trihydrochloride, serine trihydrochloride, threonine trihydrochloride, asparagine trihydrochloride, glutamine trihydrochloride, cysteine trihydrochloride, selenocystein trihydrochloride, glycine trihydrochloride, proline trihydrochloride, alanine trihydrochloride, valine trihydrochloride, isoleucine trihydrochloride, leucine trihydrochloride, methionine trihydrochloride, phenylalanine trihydrochloride, tyrosine trihydrochloride, or tryptophan trihydrochloride.

Suitable alkanolamines include, for example, monoalkanolamine, dialkanolamine, or trialkanolamine. Some examples of alkanolamines include, for example, methanolamine, ethanolamine, monoethanolamine, diethanolamine, triethanolamine, ethylaminoethanol, methylaminoethanol, dimethylaminoethanol, isopropanolamine, triethanolamine, isopropanoldimethylamine, ethylethanolamine, 2-butanolamine, or mixtures thereof.

In some embodiments, the reactants including the lysine HCl, and the ethanolamine are reacted together in the same or single reaction vessel. The lysine HCl can be added to the ethanolamine or the ethanolamine can be added to the lysine HCl. Either reaction can take place in the presence of HCl gas or the HCl gas can be added in after the lysine HCl, and the ethanolamine are mixed. In some embodiments, the lysine hydrochloride and/or ethanolamine addition comprises reacting lysine hydrochloride and ethanolamine at a molar ratio of from about 2.3 to about 1.

In some embodiments, the lysine hydrochloride can be in liquid or solid form and the ethanolamine also is in liquid form and poured into the lysine hydrochloride to form the lysine ester trihydrochloride. In some embodiments, the lysine hydrochloride can be in liquid or solid form and the ethanolamine can be in liquid form and poured into the lysine hydrochloride and heated to a temperature of from about 90° C. to about 140° C. in the presence of HCL gas to form the lysine ester trihydrochloride. In some embodiments, the lysine hydrochloride is in liquid or solid form and the ethanolamine is in liquid form and lysine hydrochloride is added to the ethanolamine to form the lysine ester trihydrochloride. In some embodiments, the lysine hydrochloride is in liquid or solid form and the ethanolamine is in liquid form and the lysine hydrochloride is added to the ethanolamine and heated to a temperature of from about 90° C. to about 140° C. in the presence of HCL gas to form the lysine ester trihydrochloride.

Isolating Amino Acid Salt

The amino acid trihydrochloride (e.g., lysine ester trihydrochloride) can be isolated and purified to the desired purity, e.g., from about 95% or from about 98% to about 99.9% by filtration, centrifugation, distillation, which separates volatile liquids on the basis of their relative volatilities, crystallization, recrystallization, evaporation can be used to remove volatile liquids from non-volatile solutes, solvent extraction can remove impurities, or can recover the desired composition by dissolving it in a solvent in which other components are soluble therein or other purification methods.

In some embodiments, the amino acid trihydrochloride (e.g., lysine ester trihydrochloride) is formed in crystal form via crystallization, which separates the amino acid trihydrochloride (e.g., lysine ester trihydrochloride) from the liquid feed stream by cooling the liquid feed stream or adding precipitants which lower the solubility of the amino acid trihydrochloride product so that it forms crystals. The solid crystals are then separated from the remaining liquor by filtration or centrifugation. The crystals can be resolubilized in a solvent and then recrystallized and the crystals are then separated from the remaining liquor by filtration or centrifugation to obtain a highly pure amino acid trihydrochloride salt. In some embodiments, the crystals can then be granulated to the desired particle size. In some embodiments, crystallization can be initiated by seeding or without seeding.

In some embodiments, the amino acid trihydrochloride (e.g., lysine ester trihydrochloride) can be purified with ethanol and/or methanol. Therefore, the reactant alkanolamine can be used with a similar alcohol solvent for purification, which reduces steps in the purification process and makes, in some embodiments, the process environmentally safer and cost effective as these reagents/solvents are easier to handle.

In some embodiments, the amino acid trihydrochloride (e.g., lysine ester trihydrochloride) can be purified where the lysine ester trihydrochloride is formed in crystalized form and dissolved in methanol and/or ethanol to form a lysine ester trihydrochloride and methanol and/or ethanol mixture and the lysine ester trihydrochloride is removed from the mixture to form a high purity recrystallized lysine ester trihydrochloride having a purity of from about 98% to about 99.99%. In some embodiments, the amino acid trihydrochloride can be recovered via filtration or vacuum filtration before or after purification.

Lysine Ester Trihydrochloride Salt Preparation

In some embodiments, the current disclosure provides a one step process for the preparation of lysine ester trihydrochloride salt, an intermediary in the production of lysine ester triisocyanate. An embodiment of lysine ester trihydrochloride salt is shown below:

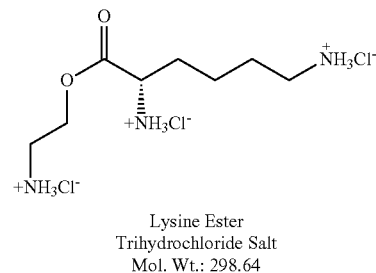

Lysine Ester
Trihydrochloride Salt
Mol. Wt.: 298.64

Lysine trihydrochloride salt had been previously prepared using a 3-step process that employed BOC-protected intermediates (BOC=Tert-butyloxycarbonyl) as shown in Scheme 1.

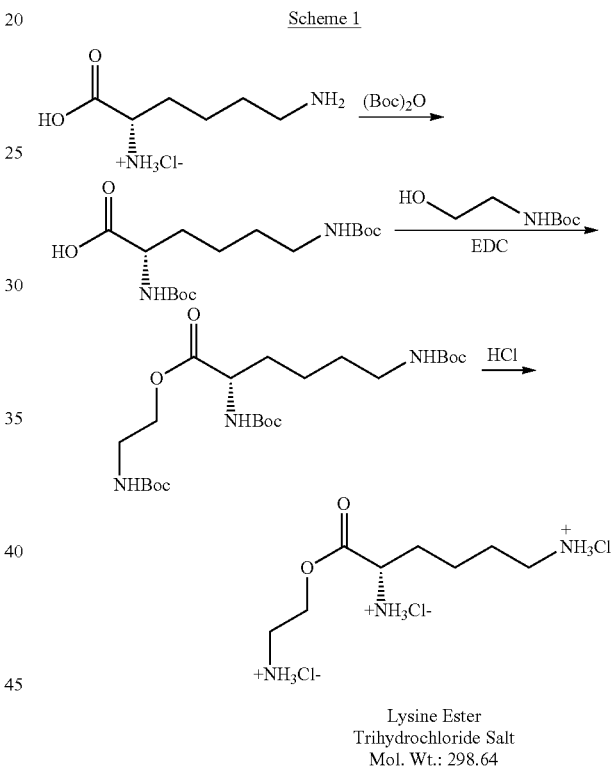

Lysine Ester
Trihydrochloride Salt
Mol. Wt.: 298.64

However, the method of preparation cannot be carried out in a single pot. Furthermore, many of the starting materials are difficult to obtain or expensive.

The lysine ester trihydrochloride salt had previously been prepared by the reaction of the trihydrochloride salt with diphosgene at 125° C. in dichlorobenzene. Diphosgene was expensive and difficult to procure, and the process required a large excess (greater than 30 molar equivalents) of phosgene due to the high reaction temperature. This resulted in the evolution of a large amount of unreacted phosgene from the reaction mixture, posing safety and containment concerns. Direct use of phosgene gas was contraindicated by the limited supply, transport, the high cost of transport, warehousing regulations, and safety measures and other considerations.

The reaction shown in Scheme 2 below was, in some embodiments, designed to take place in a single reaction vessel and uses readily available and safe reactants, such as for example lysine hydrochloride and ethanolamine. Scheme 2 depicts one embodiment of the reaction.

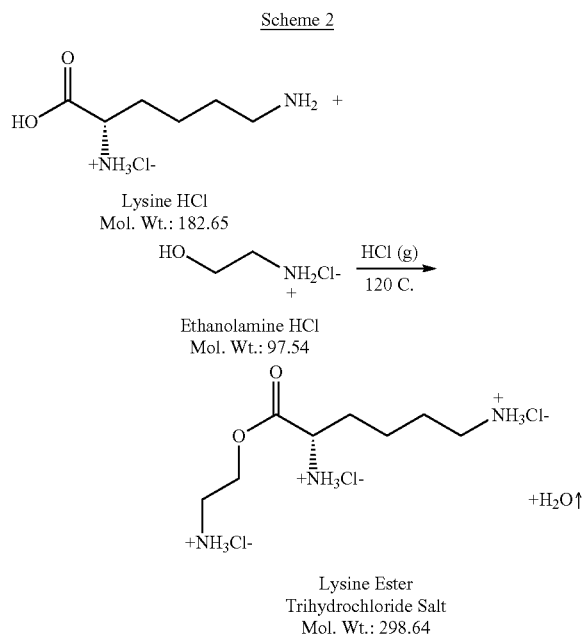

Scheme 2

Lysine HCl
Mol. Wt.: 182.65

Ethanolamine HCl
Mol. Wt.: 97.54

Lysine Ester
Trihydrochloride Salt
Mol. Wt.: 298.64

The optimized conditions developed for the one-pot or one reaction vessel synthesis process used an alkanolamine, such as, for example, ethanolamine-HCl and an amino acid monohydrochloride salt such as, for example, lysine-HCl in a molar ratio of 2.3 to 1. In some embodiments, the molar ratio of the alkanolamine to the amino acid monohydrochloride is 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, or 4:1. In one embodiment, ethanolamine was used as the hydrochloride salt in order to avoid the large exotherm encountered when a free amine was used. Furthermore, ethanolamine-HCl melts at approximately 90° C. and is used as both reactant and solvent for the reaction. The amino acid monohydrochloride such as, for example, lysine-HCl is added to the melt slowly, in portions, to form a suspension with partial dissolution.

Once the reagents were combined, in this embodiment, HCl gas is added and the container is heated to 120° C. Reaction completion is determined by consumption of lysine as observed by $^1$H NMR. Once complete, the reaction mixture was cooled slightly (90° C.) and carefully combined with an alkanol such as, for example, methanol to dissolve. Ethanol is added to the mixture to give a 30% methanol solution with a 5 ml/gram ratio of methanol to total mass. Cooling to room temperature, with seeding, produces a crystalline solid that could be recovered by vacuum filtration. The product was deliquescent and had to be handled under inert conditions to prevent uptake of moisture from the air.

Impure solids recovered from the initial isolation could be purified by repeating the methanol-ethanol recrystallization described above using the same loadings and ratios. In some embodiments, the solvents (e.g., methanol and/or ethanol) can be re-used or recycled.

Methods of Making Amino Acid Triisocyanates

The compositions and methods of making amino acid polyisocyanates include making an amino acid salt and using this salt to produce the amino acid polyisocyanate. In some embodiments, there is a method of making an amino acid triisocyanate, the method comprising reacting an amino acid trihydrochloride with phosgene to form the amino acid triisocyanate. In some embodiments, the amino acid trihydrochloride comprises lysine ester trihydrochloride salt and the amino acid triisocyanate comprises lysine ester triisocyanate.

The amino acid triisocyanate can be a triisocyanate of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or a combination thereof. The amino acid containing triisocyanate can be an ester thereof (e.g., lysine ester triisocyanate).

The amino acid triisocyanate can be made by reacting an amino acid trihydrochloride with phosgene to form the amino acid triisocyanate. Phosgene can include trichloromethyl chloroformate (diphosgene), bis(trichloromethyl) carbonate (triphosgenediphosgene) or a phosgene substitute and/or precursor can be used, which is a compound able to replace phosgene as a reagent in syntheses, or able to specifically bring about the basic phosgene functions as a carbonylating agent or a combination thereof. The phosgene can be provided in liquid or gaseous phase.

In some embodiments, the phosgene utilized in accordance with the present application may be provided via thermal dissociation of carbamic acid derivatives using chloroformates, disphenylcarbonate, or N,N'-carbonyldiimidazole.

In some embodiments, diphosgene is used and has the formula of ClCO2CCl3. Diphosgene is a colorless liquid at room temperature, and can be used as a phosgene source in many applications. Diphosgene can decompose very rapidly and quantitatively upon heating and/or upon catalysis, and the in situ generated phosgene can react with a nucleophile. In accordance with the present application, a nucleophile can be an amine including its salt form, which reacts with phosgene to produce an isocyanate.

As understood by these of ordinary skill in the art, under certain conditions, diphosgene can serve as a source of two equivalents of phosgene as shown below:

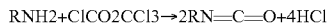

RNH2+ClCO2CCl3→2RN=C=O+4HCl

R is a substituted or unsubstituted alkyl group. In some embodiments, and preferably, triphosgene is used as a source of phosgene. In some embodiments, the phosgene used was prepared by thermal and catalytic decomposition of triphosgene into phosgene so as to provide a phosgene source or generator as shown in Scheme 4 below.

Scheme 4

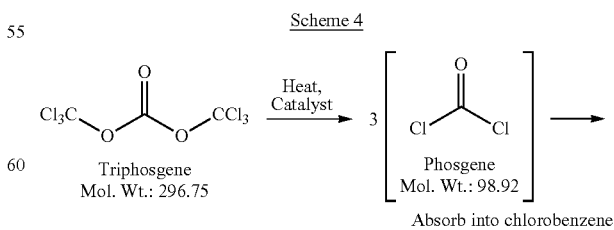

Triphosgene
Mol. Wt.: 296.75

Phosgene
Mol. Wt.: 98.92

Absorb into chlorobenzene

In some embodiments, the phosgene is obtained from triphosgene that is heated in the presence of a catalyst and recovered in chlorobenzene and/or dichlorobenzene. In some embodiments, the phosgene and/or chlorobenzene and/or dichlorobenzene is in liquid form.

Although chlorobenzene or dichlorobenzene is shown, it will be understood that any chlorinated aromatic cyclic or acyclic compound can be used.

In some embodiments, when making lysine ester triisocyanate, the boiling point of dichlorobenzene is sufficiently high that it interferes with the purification of lysine ester triisocyanate. Two separate wiped-film still distillations may be needed to remove dichlorobenzene and subsequently purify lysine ester triisocyanate. To overcome this issue, in one embodiment, chlorobenzene is used as a solvent. Chlorobenzene was shown to be equally effective and residual solvent levels could be reduced to acceptable levels by heating under high vacuum without distillation.

In one embodiment, an effective method was found by using phosgene by direct addition as a gas or, more safely and effectively, as a solution into chlorobenzene (Scheme 3). In some embodiments, the phosgene was in gas or liquid form and was trapped in chlorobenzene liquid. In some embodiments, the phosgene made up 10%, 15%, 20%, 25%, 30%, 35%, 40%, 45%, 50%, 55%, or 60% of the chlorobenzene-phosgene liquid reaction mixture. The phosgene can be added into the chlorobenzene liquid slowly so as to not build up high levels of phosgene. High levels of phosgene present in the reaction mixture reduced the reflux temperature which slows the reaction rate significantly. The highest reaction rate was observed at or above 120° C. However, temperatures of from about 100° C. to about 200° C. can be used to heat the triphosgene. The gas which evolved from the phosgene generator is trapped by formation of a solution in chlorobenzene. Very high concentrations of phosgene in chlorobenzene could be achieved (greater than 50 wt % is possible). In general, the concentration of phosgene was limited to 25 to 30 wt %. The preparation of phosgene is described in the examples. Addition of phosgene as a solution was safer since any exothermic reaction could be controlled by slowing or stopping addition of the reagent.

In some embodiments, phosgene solution is continuously added until all or nearly all the solids have disappeared, which implies reaction completion. This results in a minimum use of phosgene, leaving less phosgene to be removed and quenched as shown in Scheme 3.

Apart from the danger associated with phosgene gas, its use at lab scale presents several issues which must be overcome. Small cylinders of phosgene are expensive, difficult to procure and are limited to one or very few suppliers. For the purposes of this disclosure, the phosgene was prepared by thermal and catalytic decomposition of triphosgene directly into phosgene ("phosgene generator"), shown above in Scheme 4.

In some embodiments, the phosgene is made from the triphosgene in the presence of heat and a catalyst to produce the phosgene, which is absorbed into the chlorobenzene. In some embodiments, the catalyst used for the phosgene preparation can be cobalt phthalocyanine. In some embodiments, the catalyst used for the phosgene preparation can be phenanthroline. In some embodiments, the catalyst used for the phosgene preparation was 1,10-phenanthroline, which was reliable and repeatable. In some embodiments, both cobalt phthalocyanine and 1,10-phenanthroline are used as catalysts for the reaction.

In some embodiments, the catalyst can be added to the reaction to make the phosgene in an amount from about 0.1% to about 5%, 0.5% to about 10%, 15% to about 20%, or 25% to about 35% by weight based on the total weight of the triphosgene. In some embodiments, 1,10-phenanthroline was used to stall the cobalt phthalocyanine-catalyzed reaction and force the reaction to completion. Using this method, almost 2 kilograms of phosgene may be prepared in the lab, as a solution in chlorobenzene. NMR proved to be an effective way to monitor reaction progress by looking for the disappearance of starting trihydrochloride salt.

Isolation of Amino Acid Ester Triisocyanate

The amino acid ester triisocyanate (e.g., lysine ester triisocyanate) is isolated and purified to the desired purity (e.g., from about 95% or from about 98% to about 99.9%) by filtration, centrifugation, distillation, which separates volatile liquids on the basis of their relative volatilities, crystallization, recrystallization, evaporation, which removes volatile liquids from non-volatile solutes, solvent extraction, which can remove impurities, or recovers the desired composition by dissolving it in a solvent in which other components are more soluble therein or other purification methods.

In some embodiments, the amino acid triisocyanate (e.g., lysine ester triisocyanate) is formed in crystal form via crystallization, which separates the amino acid triisocyanate (e.g., lysine ester triisocyanate) from the liquid feed stream by cooling the liquid feed stream or adding precipitants which lower the solubility of the amino acid triisocyanate product so that the amino acid triisocyanate forms crystals. The solid crystals are then separated from the remaining liquor by filtration or centrifugation. The crystals can be resolubilized in a solvent and then recrystallized and the crystals are then separated from the remaining liquor by filtration or centrifugation to obtain a highly pure amino acid triisocyanate. In some embodiments, the crystals can then be granulated to the desired particle size. In some embodiments, the lysine ester triisocyanate is isolated in liquid form.

In some embodiments, the lysine ester triisocyanate can be isolated by triple distillation. The first distillation is for removal of residual dichlorobenzene from the lysine ester triisocyanate. The second distillation is for removal of an impurity such as, for example, diisocyanate-methyl ester. The final distillation is to isolate pure lysine ester triisocyanate (e.g., being 98% to about 99% by weight purity). However, it was observed that the recrystallization of the intermediate trihydrochloride salt developed and this gave very low levels of the methyl ester impurity (e.g., less than 1%, 0.5% or 0.25% by weight). Substitution of dichlorobenzene with chlorobenzene allowed for easy removal by high vacuum and heating. This avoided two of the previous distillations steps. Thus, the need for triple distillation was avoided and only one distillation step, in some embodiments, was utilized. Therefore, the lysine triisocyanate was made in fewer steps making the method easier and simpler.

In experiments shown in the example section, $^1$H NMR analysis indicated that the lysine ester triisocyanate product had high purity (e.g., having 95% or 98% to about 99.99% by weight purity). Treatment of the isolated oil that contained the lysine ester triisocyanate with activated carbon (to decolorize) in methyl tert-butyl ether (MTBE) solution resulted in a product of acceptable appearance and purity. Polymeric by-product impurities were found to be insoluble in MTBE and were easily removed during filtration of the carbon. In this manner, distillation of the final product was eliminated from the process.

In some embodiments, a method of making the amino acid triisocyanate is provided where the amino acid ester triisocyanate (e.g., lysine ester triisocyanate) is distilled to remove chlorobenzene and/or dichlorobenzene to form a distilled amino acid triisocyanate in one, two, three, four, or five distilling steps. In some embodiments, a method of making the amino acid triisocyanate is provided where the amino acid ester triisocyanate (e.g., lysine ester triisocyanate) is distilled to remove chlorobenzene and/or other impurities to form a distilled amino acid triisocyanate in one distillation step, where the amino acid ester triisocyanate (e.g., lysine ester triisocyanate) is formed and isolated in one reaction vessel.

In some embodiments, the lysine ester triisocyanate obtained has at least 95% by weight purity. In other embodiments, lysine ester triisocyanate obtained has at least 50%, 55%, 60%, 65%, 70%, 75%, 80%, 85%, 90%, 95%, or 99.5% by weight purity.

In some embodiments, the amino acid ester triisocyanate (e.g., lysine ester triisocyanate) can be purified where the lysine ester triisocyanate is formed in crystalized form in a solvent and then removed from the solvent to form a high purity lysine ester triisocyanate having a purity of from about 95% or from about 98% to about 99.99%. In some embodiments, the amino acid ester triisocyanate (e.g., lysine ester triisocyanate) can be recovered via filtration or vacuum filtration before or after purification.

In some embodiments, methodologies, tools and/or reagents utilized in accordance with the present application are used in synthesis of isocyanates, which includes multi-isocyanate compounds. Exemplary multi-isocyanate compounds include, but are not limited to, lysine diisocyanate, an alkyl ester of lysine diisocyanate (for example, a methyl ester or an ethyl ester), lysine triisocyanate, an alkyl ester of lysine triisocyanate (for example, a methyl ester or an ethyl ester), lysine triisocyanate, dimers prepared form aliphatic polyisocyanates, trimers prepared from aliphatic polyisocyanates and/or mixtures thereof.

Use of Isocyanates

Isocyanates formed by methods in accordance with the present application, can be purified and used to form urethane linkage with a hydroxyl functional group. For example, if a component having two or more hydroxyl groups (i.e., polyols) is reacted with an isocyanate containing two or more isocyanate groups (i.e., polyisocyanate), polymer chains are formed, known as polyurethane (PUR).

Polyurethanes can be made by reacting together the components of a two-component composition, one of which includes a polyisocyanate and a polyol. It is to be understood that by "a two-component composition" it means a composition comprising two essential types of polymer components. In some embodiments, such a composition may additionally comprise one or more other optional components.

An exemplary reaction for polyurethane synthesis using lysine ester triisocyanate is illustrated below, where an isocyanate and a polyester polyol react to form urethane bonds. In some embodiments, R1, R2 and R3, are respectively, oligomers of caprolactone, lactide and glycolide. A typical reaction forming polyurethane is shown below.

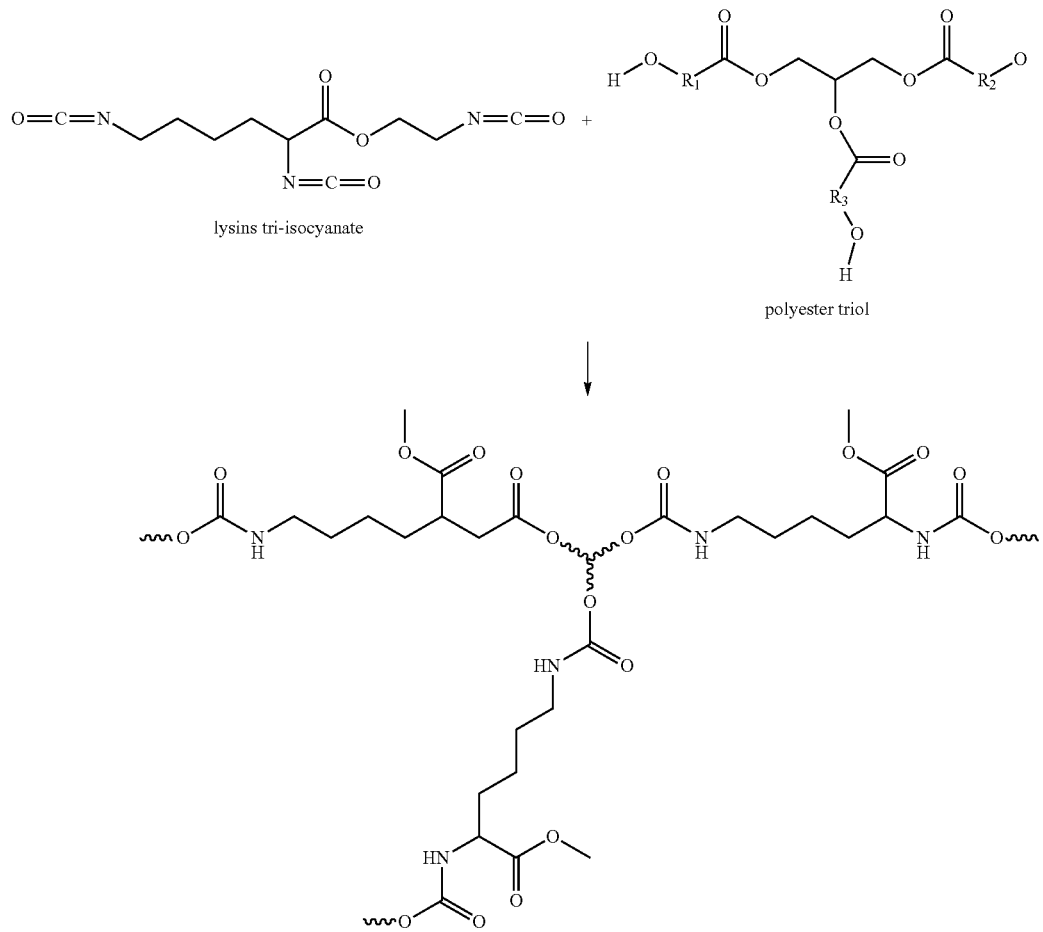

Depending on reaction conditions, a product of reacting an isocyanate with a polyol can be a polymer that is fully polymerized, or a pre-polymer that can be further polymerized. In some embodiments, a pre-polymer produced from an isocyanate is used in a two-component composition to make polyurethane materials. A pre-polymer is a low molecular weight oligomer typically produced through stepwise growth polymerization. For example, a polyol and an excess of polyisocyanate may be polymerized to produce isocyanate terminated prepolymer that may be combined then with a polyol to form a polyurethane. In some embodiments, a polyol reacted with an excess of polyisocyanate to make a pre-polymer, includes, but is not limited to, polyethylene glycol, glycerol, pentaerythritol, dipentaerythritol, tripentaerythritol, 1,2,4-butanetriol, trimethylolpropane, 1,2,3-trihydroxyhexane, myo-inositol, ascorbic acid, a saccharide, or sugar alcohols (e.g., mannitol, xylitol, sorbitol etc.).

In some embodiments, a polyol or polyamine is used in making the prepolymer. In some embodiments, the polyol used to make the pre-polymer, is a polyol containing more than one hydroxyl groups, such as polyethylene glycol (PEG), glycerol, pentaerythritol, dipentaerythritol, tripentaerythritol, 1,2,4-butanetriol, trimethylolpropanol, 1,2,3-trihydroxyhexanol, myo-inositol, or sugar alcohols (e.g., mannitol, xylitol, sorbitol etc.) or a combination thereof.

In some embodiments, the polyol comprises glycerol or glycerin, tetramethylolmethane, trimethylolethane (for example 1,1,1-trimethylolethane), trimethylolpropane (TMP) (for example 1,1,1-trimethylolpropane), caprolactone, glucose derivatives, sorbitol, erythritol, branched or unbranched pentaerythritol, dipentaerythritol, tripentaerythritol, sorbitan, alkoxylated derivatives or a combinations thereof. Suitable branched pentaerythritols may include pentaerythritol ethoxylate or pentaerythritol propoxylate, or combinations thereof, or the like.

In some embodiments, the polyol comprises methoxypolyethylene glycol, polyethylene glycol, polypropylene glycol, polybutylene glycol, polytetramethylene glycol, polyhexamethylene glycol, trimethylene carbonate, $\epsilon$-caprolactone, p-dioxanone, glycolide, lactide, 1,5-dioxepan-2-one, polybutylene adipate, polyethylene adipate, polyethylene terephthalate, polyethylene glycol-polycaprolactone, polyethylene glycol-polylactide, polyethylene glycol-polyglycolide, glycolide-polyethylene glycol-caprolactone copolymers, aliphatic oligoesters, or combinations.

In some embodiments, the polyol comprises a reactive molecule which contains at least two functional groups that are capable of reacting with an isocyanate group. Most polyols suitable for use in the biocompatible and biodegradable polyurethanes of the present application are amine- and/or hydroxyl-terminated compounds and include, but are not limited to, polyether polyols (such as polyethylene glycol (PEG or PEO), polytetramethylene etherglycol (PTMEG), polypropylene oxide glycol (PPO)); amine-terminated polyethers; polyester polyols (such as polybutylene adipate, caprolactone polyesters, castor oil); and polycarbonates (such as poly(1,6-hexanediol) carbonate). In some embodiments, the biocompatible and biodegradable polyurethanes of the present application include biocompatible and biodegradable polyols such as, for example, lactone-based polyesters (such as poly($\epsilon$-caprolactone)) and polyethylene glycol. In some embodiments, particularly preferred polyols include, but are not limited to: (1) biomolecules having multiple hydroxyl or amine functionality, such as glucose, polysaccharides, or castor oil; or (2) biomolecules (such as fatty acids, triglycerides, and phospholipids) that have been hydroxylated by known chemical synthesis techniques to yield polyols.

In some embodiments, polyols to be reacted with the polyisocyanate have a molecular weight of no more than 1000 g/mol. In some embodiments, polyols have a range of molecular weight between about 100 g/mol to about 500 g/mol. In some embodiments, polyols have a range of molecular weight between about 200 g/mol to about 1000 g/mol. In certain embodiments, polyols (e.g., PEG) have a molecular weight of between about 200 g/mol to about 400 g/mol. For example, a lysine ester triisocyanate-PEG prepolymer can be made using PEG-200 (i.e., having an average molecular weight of 200 g/mol).

In some embodiments, reacting a polyisocyanate with a polyol or polyamine can result in a mixture of products. For example, polyurethane materials can be produced by reacting at least one isocyanate with at least one polyol. A product can refer to a composition formed by the reaction of an isocyanate (e.g., lysine triisocyanate) and a polyol (e.g., PEG). In some embodiments, a product can include a series of polymer materials having a distribution of various molecular weights.

In some embodiments, the polyisocyanate is reacted with a polyamine to form the polyurethane. In some embodiments, the polyamine can have the monomer having the formula I NH2-R1-CH(NH2)CO—OR2-NH2, wherein R1 and R2, respectively and independently, represent an aliphatic or an aryl group or R1 and R2 can be the same or different substituted or unsubstituted alkyl moiety.

Amines used in accordance with the present application may include an aliphatic amine, an aromatic amine, a salt form thereof, or any combinations thereof. Polyamines have two or more amino functional groups. In some embodiments, the polyamine comprises at least one primary amine to generate the polyisocyanate. In some embodiments, the polyamine comprises two or three primary amino groups.

As defined generally above, the R1 and/or R2 moieties of formula I can be any aliphatic or aryl group. In some embodiments, the R1 moiety of formula I is an aliphatic group. In some embodiments, the R2 moiety of formula I is an aliphatic group. In some embodiments, the R1 moiety of formula I is an aryl group. In some embodiments, the R2 moiety of formula I is an aryl group.

In some embodiments, the R1 and R2 moieties of formula I are both aliphatic groups. In some embodiments, the R1 and R2 moieties of formula I are both aryl groups. In certain embodiments, the R1 and R2 moieties of formula I are different groups, respectively. In still other embodiments, the R1 and R2 moieties of formula I are the same groups.

In some embodiments, the R1 moiety of formula I is —(CH2)4.

In some embodiments, the R2 moiety of formula I is —(CH2)2.

In some embodiments, the R1 moiety of formula I is —(CH2)4 and the R2 moiety of formula I is —(CH2)2.

In some embodiments, the R1/R2 moiety of the formula I is an optionally substituted aliphatic group, as described above. Examples of the R1/R2 moiety include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said R1/R2 moiety is an optionally substituted alkyl group. In other embodiments, said R1/R2 moiety is an optionally substituted alkynyl or alkenyl group. When said R1/R2 moiety is a substituted aliphatic group, suitable substituents on R1/R2 include CN, N3, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the R1 group is 2-(N-methyl-N-(ethynylcarbonyl)amino)ethoxy, 4-ethynylbenzyloxy, or 2-(4-ethynyl-phenoxy)ethoxy.

In certain embodiments, the R1/R2 moiety of formula I is an optionally substituted aryl group, as described above. Examples include optionally substituted phenyl and optionally substituted pyridyl. When said R1/R2 moiety is a substituted aryl group, suitable substituents on R1/R2 include CN, N3, NO2, —CH3, —CH2N3, —CH═CH2, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl or a combination thereof. In some embodiments, the polyamine comprises putrescine or a phosphoester polyamine.

Polyurethanes (PUR) can be included with other material as part of composite materials, for example, with bone particles as described in U.S. Pat. No. 7,985,414, the contents of which is incorporated herein by reference. Such composite materials may be prepared by contacting an isocyanate-terminated prepolymer (e.g., a lysine ester triisocyanate-PEG pre-polymer) with a polyol (e.g., a polyester polyol) or polyamine, and optionally with addition of water, a catalyst, a stabilizer, a porogen, PEG, an agent to be delivered to form the polyurethane.

In one embodiment, a polyurethane composite includes a polyurethane formed by reaction of a polyisocyanate such as, for example, lysine ester triisocyanate, with a hydroxylated or aminated material (e.g., polyol, polyamine, etc.). In one embodiment, the composite includes and included material, e.g., a biomolecule, extracellular matrix component, bioactive agent, small molecule, tissue-derived material, inorganic ceramic, bone substitute, a composite of an inorganic ceramic with one or more of a tissue-derived material, extracellular matrix material, or sugar (e.g., sucrose, dextrose, etc.) bovine serum albumin, or a mixture thereof.

The included material (e.g., bioactive agent, additional agent, bone material, etc.) in some embodiments, can be contacted with the polyol or polyamine and then reacted with the polyisocyanate. The included material (e.g., bioactive agent, additional agent, bone material, etc.) in some embodiments, can be contacted with the polyisocyanate and then reacted with the polyol or polyamine. The included material (e.g., bioactive agent, additional agent, bone material, etc.) in some embodiments, can be contacted with both the polyol or polyamine and the polyisocyanate. In some embodiments, after the polyol or polyamine and the polyisocyanate are mixed, then the included material can be mixed with the prepolymer or the forming polyurethane.

In some embodiments, polyurethanes are often formed by the reaction of a polyisocyanate (such as a diisocyanate or a triisocyanate) with a polyol (such as a diol) as shown below:

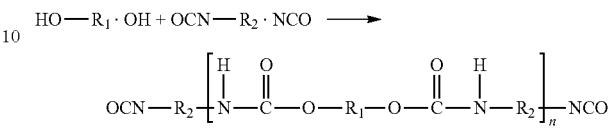

Polyurethanes may be straight chains or branched, and may have high or low molecular weights. Polyurethanes may also contain urea linkages formed by the reaction of an isocyanate with an amine. In an alternative embodiment, polyurethanes are formed by reacting a polyol or polyamine with an excess of polyisocyanate to form a macropolyisocyanate prepolymer, following which the prepolymer is reacted with a second polyol or polyamine to form the polyurethane as shown below:

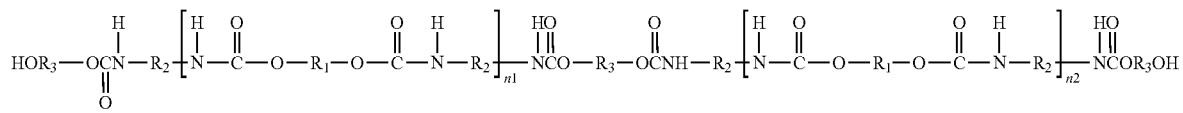

The R1, R2, and R3 groups, which can be substituted and unsubstituted alkyl groups, cyclic and non-cyclic groups, provide great flexibility in tailoring the mechanical and chemical properties of polyurethanes, which may be made rigid, soft, plastic, and/or elastomeric by selection of appropriate functional groups, where n is the number of monomeric units in the polymer. The use of R groups having different types of chemical linkages creates regions of the polyurethane that are more and less flexible. For example, aromatic and polyaromatic R groups increase the rigidity of that segment of the polymer, while alkane and polyol chains are relatively flexible. The mixture of rigid, or hard, with flexible, or soft, segments in a polyurethane results in a strong, tough, elastomeric material. The ratio of hard and soft segments may be adjusted to optimize the mechanical properties of the composite.

Exemplary polyols and polyamines include but are not limited to degradable polyesters such as polylactide and polyglycolide and their copolymers, amino acid oligomers including hydroxylated or aminated residues, polyether polyols, e.g., polyethylene glycol and polypropylene glycol, polytetramethylene ether glycol, hydroxylated or aminated hydrocarbons, hydroxybutyl or butylamine terminated polydimethylsiloxanes, polydimethylsiloxane glycol, polycaprolactones, polyhydroxybutyrate, polyhydroyvalerate, polycarbonates, tyrosine-based polycarbonates, polytetramethylene oxide, myoinisitol (a pentahydroxy sugar), poly(glycolide-co-d-caprolactone), glycerol, ethylene glycol copolymers, DIOREZ™ (a commercially available polyester polyol), PLURONICS™ polymers, polyethylene oxide, polypropylene oxide, hydroxyl or amine terminated poly(1,4-butadiene), hydrogenated or aminated polybutadiene, ethylene diamine, phenylalanine-based esters (see U.S. Pat. No. 6,221,997), adipic acid, hydroxyl or amine terminated polyisobutylene, polyhexamethylene carbonate glycol, amine-terminated polyethers; polyester polyols (such as polybutylene adipate, polyethylene adipate, polytetramethylene adipate caprolactone polyesters, castor oil); and polycarbonates (such as poly(1,6-hexanediol) carbonate), and copolymers of any of these. In some embodiments, the polyol or polyamine has a molecular weight of about 400 to about 5000.

Exemplary chain extenders that can be used in the polyurethane composition include but are not limited to 1,4-cyclohexane dimethanol, polyols of polyhydroxybutyrate or polyhydroxyvalerate, putrescine, polylactide, polyglycolide, poly(lactide-co-glycolide), biocompatible diester diols and diurea diols, 1,4-butanediol, ethylene diamine, 4,4'-methylene bis (2-chloroaniline), ethylene glycol, 3-hexyne-2,5-diol, 2-amino-1-butanol, or hexanediol or other aromatic and aliphatic diols or diamines.

In some embodiments, R1, R2, or R3 of the formula above may include alkyl, aryl, heterocycles, cycloalkyl, aromatic heterocycles, multicycloalkyl, hydroxyl, ester, ether, carboxylic acid, amino, alkylamino, dialkylamino, trialkylamino, amido, alkoxy, or ureido groups. Alternatively or in addition, R1, R2, or R3 may also include branches or substituents including alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl, thioether, thiol, alkoxy, or ureido groups. Exemplary groups for use as R1, R2, or R3 also include bioactive agents, biomolecules, and small molecules. Appropriate polyurethanes also include those disclosed in U.S. Patent Publication No. 2005/0013793, the contents of which are incorporated herein by reference.

In some embodiments, polyurethane composites are formed by reacting an appropriate polyisocyanate crosslinker (e.g., a triisocyanate) or macropolyisocyanate prepolymer with an aminated or hydroxylated material to form composites which may have osteogenic and/or osteoinductive properties. Of course, the material may have both amine and hydroxyl groups. The composites also may incorporate an included material, for example, a biomolecule, extracellular matrix component, bioactive agent, small molecule, bone, bone substitute, tissue derived material, inorganic ceramic, or a mixture of these. Details of traditional polyurethane synthesis can be found, for example, in Lamba, et al., Polyurethanes in Biomedical Applications, CRC Press, 1998, which is incorporated herein by reference, and particularly in Chapter 2 of the above reference. The hydroxylated or aminated material may serve as a polyol/polyamine in a macropolyisocyanate, as a chain extender, or as any of R1, R2, or R3.

Naturally derived materials may also be used as polyols or polyamines and may serve as part of the macropolyisocyanate, the chain extender, or both. In one embodiment, the hydroxylated or aminated material is a biomolecule, for example, a lipid (e.g., phospholipid, lecithin, fatty acid, triglyceride, or cholesterol) or polysaccharide (e.g., oligosaccharide or amylase-resistant starches). A biomolecule for use according to the techniques of the present application may be hydroxylated by any method known to those skilled in the art if it does not already possess sufficient reactive groups to carry out a reaction. For example, lipids, including phospholipids, mono-, di-, and triglycerides, fatty acids, and cholesterols may require addition of hydroxyl or amine groups in order to carry out the polymerization reaction. In contrast, many polysaccharides already have sufficient hydroxyl groups to polymerize readily into a highly cross-linked polymer.

The hydroxylated or aminated material may also include intact extracellular matrix (ECM), its components, alone or in combination, or modified or synthetic versions thereof. These materials may be treated to increase the concentration of hydroxyl and/or amino groups, especially the surface concentration of these groups. For example, collagen may be decross-linked or treated with lysyl oxidase. Lysyl oxidase converts the terminal amino groups of lysine to aldehydes, which may then be reduced. Alternatively or in addition, the biomolecule, or ECM component, or tissue may be aminated. The amino groups will be incorporated into the polymer through a urea linkage. Of course, many ECM derived materials already contain primary amino groups.

Exemplary extracellular matrix components suitable for use with the present application include but are not limited to collagen, laminin, elastin, proteoglycans, reticulin, fibronectin, vitronectin, glycosaminoglycans, and other basement membrane components. Various types of collagen (e.g., collagen Type I, collagen Type II, collagen Type IV, etc., as well as collagen derived or denatured materials such as gelatin) are suitable for use with the present application. Collagens may be used in fiber, gel, or other forms. Sources for extracellular matrix components include, but are not limited to, skin, tendon, intestine and dura mater obtained from animals, transgenic animals and humans. Collagenous tissue can also be obtained by genetically engineering microorganisms to express collagen as described, e.g., in U.S. Pat. No. 5,243,038, the entire contents of which are incorporated herein by reference. Procedures for obtaining and purifying collagen typically involve acid or enzyme extraction as described, e.g., in U.S. Pat. No. 5,263,984, the contents of which are incorporated by reference herein. The polyurethane matrix may include synthetic ECM analogs. Exemplary synthetic ECM analogs include RGD-containing peptides, silk-elastin polymers produced by Protein Polymer Technologies (San Diego, Calif.) and BioSteel™, a recombinant spider silk produced by Nexia Biotechnologies (Vaudrevil-Dorion, QC, Canada). Various types of collagen (e.g., collagen Type I, collagen Type II, collagen Type IV) are also suitable for use with embodiments of the present application.

The polyurethane matrix may also include tissues, including but not limited to xenograft, allograft, or autograft tissues, including non-bony tissues and bone-derived tissues, may be used with the present application. Non-bony tissues suitable for use with the application include connective tissue such as tendon, ligament, cartilage, endodermis, small intestinal submucosa, skin, and muscle. The tissues may be excised and cut into a plurality of elongated fragments or particles employing methods known in the art. Reduction of the antigenicity of allogeneic and xenogeneic tissue can be achieved by treating the tissues with various chemical agents, e.g., extraction agents such as monoglycerides, diglycerides, triglycerides, dimethyl formamide, etc., as described, e.g., in U.S. Pat. No. 5,507,810, the contents of which are incorporated by reference herein. Small intestine submucosa tissue can be obtained and processed as described in U.S. Pat. No. 4,902,508, the contents of which are incorporated by reference herein. In summary, intestinal tissue is abraded to remove the outer layers, including both the tunica serosa and the tunica muscularis and the inner layers, including at least the luminal portion of the tunica mucosa. The resulting material is a whitish, translucent tube of tissue approximately 0.1 mm thick, typically consisting of the tunica submucosa with the attached lamina muscularis mucosa and stratum compactum. The tissue may be rinsed in 10% neomycin sulfate before use. Tissues may be modified by demineralization, amination, or hydroxylation before use. For example, lysine groups may be modified with lysyl oxidase as described above.

Ceramics may also be included in the polyurethane before, during or after it is made. Ceramics including calcium phosphate materials and bone substitute materials, may also be exploited for use as particulate inclusions or as the hydroxylated or aminated material that can be in the polyurethane matrix. Exemplary inorganic ceramics for use with the present application include calcium carbonate, calcium sulfate, calcium phosphosilicate, sodium phosphate, calcium aluminate, calcium phosphate, hydroxyapatite, alpha and/or beta tricalcium phosphate, dicalcium phosphate, tetracalcium phosphate, amorphous calcium phosphate, octacalcium phosphate, or BIOGLASS™, a calcium phosphate silica glass available from U.S. Biomaterials Corporation. Substituted CaP phases are also contemplated for use with the present application, including but not limited to fluorapatite, chlorapatite, Mg-substituted tricalcium phosphate, and carbonate hydroxyapatite. Additional calcium phosphate phases suitable for use with the present application include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, On Biomineralization, Oxford University Press, 1989, incorporated herein by reference. The composite may contain between about 5% and 80% bone-derived or other ceramic material, for example, between about 20% to about 60%, or between about 30% to about 50% bone-derived or other ceramic material.

In some embodiments, a composite material may be reacted with a macropolyisocyanate to form a polyurethane composite. For example, inorganic ceramics such as those described above or bone-derived materials may be combined with proteins such as BSA, collagen, or other extracellular matrix components such as those described above to form a composite. Alternatively or in addition, inorganic ceramics or bone-derived materials may be combined with synthetic or naturally-derived polymers to form a composite using the techniques described in our co-pending application Ser. No. 10/735,135, filed Dec. 12, 2003, Ser. No. 10/681,651, filed Oct. 8, 2003, and Ser. No. 10/639,912, filed Aug. 12, 2003, the contents of all of which are incorporated herein by reference. These composites may be lightly demineralized as described below to expose the organic material at the surface of the composite before they are formed into polyurethane composites according to the teachings of the present application.

Particulate materials for use with an embodiment of the present application may be modified to increase the concentration of amino or hydroxyl groups at their surfaces using the techniques described elsewhere herein. Particulate materials may also be rendered more reactive through treatment with silane coupling reagents, such as those described in our co-pending application, published as U.S. Patent Publication No. 20050008620, the entire contents of which are incorporated herein by reference. Coupling agents may be used to link polyisocyanate, polyamine, or polyol molecules to the particle or simply to attach individual amine, hydroxyl or isocyanate groups. The linked molecules may be monomeric or oligomeric.

When the hydroxylated or aminated material is difunctional, reaction with a triisocyanate generally produces a polyurethane with minimal crosslinking. Such polymers are generally thermoplastic and readily deformable and may be subjected to strain-induced crystallization for hardening. In contrast, if at least some reactants include at least three active groups participating in the reaction, then the polymer will generally be heavily cross-linked. Such polymers are often thermosets and tend to be harder than polymers with low cross-linking. In addition, their mechanical properties tend to be less dependent on how they are processed, which may render them more machinable. Cross-linking may also be controlled through the choice of catalyst. Exemplary catalysts include mild bases, strong bases, sodium hydroxide, sodium acetate, tin, and triethylene diamine-1,4-diaza(2,2,2)bicyclooctane. The stoichiometry and temperature of the reaction may also be adjusted to control the extent of crosslinking.

Because the reaction process combines an isocyanate with a biomolecule or other biological or biocompatible material, many possible breakdown products of the polymer according to certain embodiments are themselves resorbable. In one embodiment, byproducts of enzymatic degradation, dissolution, bioerosion, or other degradative processes are biocompatible. These byproducts may be utilized in or may be metabolites of any cellular metabolic pathway, such as but not limited to cellular respiration, glycolysis, fermentation, or the tricarboxylic acid cycle. In one embodiment, the polyurethanes of the present application are themselves enzymatically degradable, bioerodable, hydrolyzable, and/or bioabsorbable. Thus, when an osteoimplant is formed from the materials of the present application, it can be slowly replaced by the ingrowth of natural bone as the implant degrades. This process of osteogenesis may be accelerated, for example, by the addition of bioactive agents. Such bioactive agents may be incorporated into the polymer structure, either as backbone elements or as side groups, or they may be present as solutes in the solid polymer or as non-covalently bonded attachments or they may be part of the polyurethane when it is formed. In any case, they may be gradually released as the polyurethane degrades. The rate of release may be tailored by modifying the attachment or incorporation of the bioactive agents into the polymer. Bioactive agents that may be used include not only agents having osteogenic properties, but also agents having other biological properties such as immunosuppression, chemoattraction, antimicrobial properties, etc.

Exemplary bioactive agents include bone stimulating peptides such as RGD, bone morphogenic proteins, and other growth factors, antibiotics, etc. Lectins are a class of particular interest for incorporation into the present polymers, especially when the polymers comprise carbohydrates, which bond readily to lectins.

In some embodiments, the biodegradable matrix can comprise sugar (e.g., dextrose, sucrose, etc.) and/or bone particles or bone substitute materials as described in U.S. Pat. No. 7,985,414. The entire disclosure of this reference is herein incorporated by reference into the present disclosure.

For certain applications, it may be desirable to create foamed polyurethane, rather than solid polyurethane. While typical foaming agents such as hydrochlorofluorocarbons, hydrofluorocarbons, or pentanes may not be biocompatible for many systems, other biocompatible agents may be used. For example, water, and ascorbic acid may be an adequate foaming agent for a lysine triisocyanate/PEG/glycerol polyurethane. Other foaming agents include dry ice or other agents that release carbon dioxide or other gases into the composite. Alternatively, or in addition, salts may be mixed in with the reagents and then dissolved after polymerization to leave behind small voids.

Whether foamed or solid, polyurethanes may be formed with an additional, included material. Exemplary included materials include but are not limited to bone-derived tissue, non-bone derived tissue, and ceramics and bone substitute materials. In some embodiments, settable osteogenic materials (e.g. alpha-BSM, available from ETEX Corp, Cambridge, Mass., Norian SRS, (Skeletal Repair System) available from Norian Corp, Cupertino, Calif., or Dynaflex, available from Citagenix) is included in the polyurethane composite. These materials may bond strongly to the polyisocyanates used in forming the polymer, since they contain or may be modified to contain significant numbers of active hydroxyl groups. Thus, it may be preferred in some embodiments to first mix the included material with the hydroxylated or aminated material, before addition of the polyisocyanate. Nevertheless, it is also within the scope of the present application to mix the additional material into already-combined hydroxylated or aminated material and polyisocyanate, or to combine all three components simultaneously. The amount of included material in the composite will vary depending on the desired application, and practically any amount of material, for example, at least 10, at least 30, at least 50, or at least 70% of the composite may be formed from the included material.

Of course, the included material may serve as the hydroxylated or aminated material. That is, materials such as biomolecules, extracellular matrix components, bioactive agents, small molecules, tissue-derived materials, inorganic ceramics, bone substitutes, and composites, such as those described above, of inorganic ceramics or bone derived materials with synthetic or naturally derived materials, extracellular matrix material, and bovine serum albumin may react with the polyisocyanate to form a polyurethane composite. In some embodiments, it may be desired to form a prepolymer of isocyanate-terminated polyurethane oligomers and react these with the included material to form the composite to add flexibility to the polymer matrix.

In some embodiments, the polyurethane matrix comprises a plurality of pores to allow ingrowth of tissue (e.g., bone tissue) to repair bone. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the biodegradable polyurethane or polyurea matrix comprises pore sizes from about 0.01 microns to about 1 mm or from about 0.02 microns to about 2 mm.

In some embodiments, the polyurethane matrix of the present application comprises a wet compressive strength of at least about 1 MPa to about 150 MPa, at least about 3 MPa to about 100 MPa, at least about 5 MPa to about 80 MPa, at least about 10 MPa to about 70 MPa at least about 20 MPa to about 60 MPa, or at least about 30 MPa to about 50 MPa.

These and other aspects of the present application will be further appreciated upon consideration of the following Examples, which are intended to illustrate certain particular embodiments of the application but are not intended to limit its scope, as defined by the claims.

EXAMPLES

Example 1

Lysine Ester Trihydrochloride Salt Production

Ethanolamine hydrochloride (1240 grams, 12.6 moles) was placed into a resin kettle fitted with mechanical stirrer, thermocouple, gas inlet tube and vacuum fitting. The solids were heated to approximately 90° C., where a melt was formed. Lysine mono-hydrochloride (1010 grams, 5.5 moles) was added in portions to the melt so as to maintain a free-flowing slurry. After the addition was complete, a vacuum (water aspirator) was established over the reaction mixture and the temperature was increased to 120° C. At the same time, HCl gas was bubbled into the reaction mixture. The rate was not measured but was estimated as 50-100 ml/min over a total addition time of about 5 hours. A significant exotherm was observed, reaching a maximum temperature of 132° C. The reaction mixture became a progressively thinner suspension as the temperature rose and eventually became a viscous, clear honey-colored oil.

Once the reaction was complete (disappearance of lysine by 1H NMR), the mixture was cooled to 90° C. and cautiously diluted with methanol (5 liters) to give a solution. During the addition of methanol the solution cooled to the reflux temperature. This hot solution was further diluted with denatured ethanol (SDA 2B-4) to a total volume of approximately 17 liters (approximately 30 volume percent methanol). Solids formed on slow cooling overnight, which were isolated by vacuum filtration. The solids were deliquescent and had to be protected from exposure to air to avoid picking up moisture. The recovery was 1420 grams (86% yield).

The trihydrochloride salt was purified by dissolving in methanol and subsequent dilution with ethanol near reflux temperature using the same ratios and loadings described above. In this manner, the product was isolated as a white, crystalline solid. Mass recovery was 1040 grams (65% yield). Additional product formed in the mother liquors over time, but was not recovered. FIG. 1 is a graphic illustration of the $^1$H NMR data obtained from isolated and purified lysine ester trihydrochloride salt. The lysine ester trihydrochloride salt had high purity (e.g., greater than 98%).

Results and Discussion

The optimized conditions developed for the one reaction vessel synthesis used ethanolamine-HCl and lysine-HCl in a molar ratio of 2.3 to 1. Ethanolamine was used as the hydrochloride salt in order to avoid the large exotherm encountered when the free amine was used. Furthermore, ethanolamine-HCl conveniently melted at approximately 90° C. and could be used as both reactant and solvent for the reaction. By adding the lysine-HCl to the melt slowly, in portions, a suspension could be formed with partial dissolution. A solid mass would form if the lysine-HCl and ethanolamine-HCl reagents were combined then heated or if the lysine-HCl was added too quickly.

Once the reagents were combined, addition of HCl gas and heating to 120° C. resulted in a clear, viscous honey-colored solution. Reaction completion was determined by consumption of lysine as observed by 1H NMR. Once complete, the reaction mixture was cooled slightly (90° C.) and carefully combined with methanol to dissolve it. Ethanol was added to the mixture to give a 30% methanol solution with a 5 ml/gram ratio of methanol to total mass. Cooling to room temperature, with seeding, produced a crystalline solid that could be recovered by vacuum filtration. The product was deliquescent and had to be handled under inert conditions to prevent uptake of moisture from the air.

Impure solids recovered from the initial isolation could be purified by repeating the methanol-ethanol recrystallization described above using the same loadings and ratios. Lysine ester trihydrochloride salt that had a high purity was produced.

Example 2

Phosgene/Chlorobenzene Solution

Triphosgene (100 grams, 0.33 moles) was placed in a reaction flask fitted with a magnetic stir bar, expansion bulb (to control foaming) and thermocouple. To this was added 1,10-phenanthroline (500 mg) and the reactor was sealed. A tube was run to another flask containing chlorobenzene (250 grams) and the tube tip was submerged in the fluid. This flask was fitted with a dry ice condenser and outlet to a sodium hydroxide scrubber. The flask was cooled in an ice-bath.

The flask containing the triphosgene was heated slowly to a maximum of 105° C. At approximately 80° C., the triphosgene melted and gas generation was observed, which was absorbed in the chlorobenzene. The reaction became more vigorous as it warmed and eventually was evolving a heavy, steady stream of gas. The reaction never appeared to become uncontrollable. After 10 to 15 minutes, the triphosgene was completely consumed and left only a dry residue. The generation could be repeated by simply adding fresh triphosgene and starting the heat cycle again. Conversion appeared to be quantitative.

The maximum scale at which this methodology was run was 250 grams of triphosgene, solely to limit the amount of phosgene generated at any one time. There were no issues observed that would limit it to this scale. Phosgene badges were used to monitor exposure (less than 1 ppm/min maximum) and full face respirators with acid cartridges were used for limited time exposure.

Example 3

Lysine Triisocyanate

A solution of phosgene in chlorobenzene (970 grams of phosgene in 2200 grams total 9.8 moles, 6 molar equivalents) was prepared. Lysine ester trihydrochloride salt (500 grams, 1.67 moles) was charged to a flask fitted with a mechanical stirrer, thermocouple and dry ice condenser. The reactor outlet was attached to a scrubber. Chlorobenzene (5 liters) was charged and a suspension formed. The mixture was heated to 120° C. and then the phosgene solution was added slowly via pump (approximately 10 ml/min). After 45 minutes of addition, some phosgene reflux was noted in the condenser. The reaction temp dropped to approximately 115° C. Addition was stopped and the temperature increased to 120° C. Addition was resumed, intermittently, to maintain a reaction temperature above 115° C. The reaction was heated for 11 hours then stopped. 1H NMR analysis showed complete conversion to LTI. The solvent was removed under reduced pressure giving a viscous amber oil. The oil was placed on rotary evaporator and heated to 65° C. at 0.9 mm Hg overnight. The chlorobenzene level had dropped to 77 ppm, but the material had darkened significantly. Mass recovery was 370 grams (83% yield).

Figure 2:
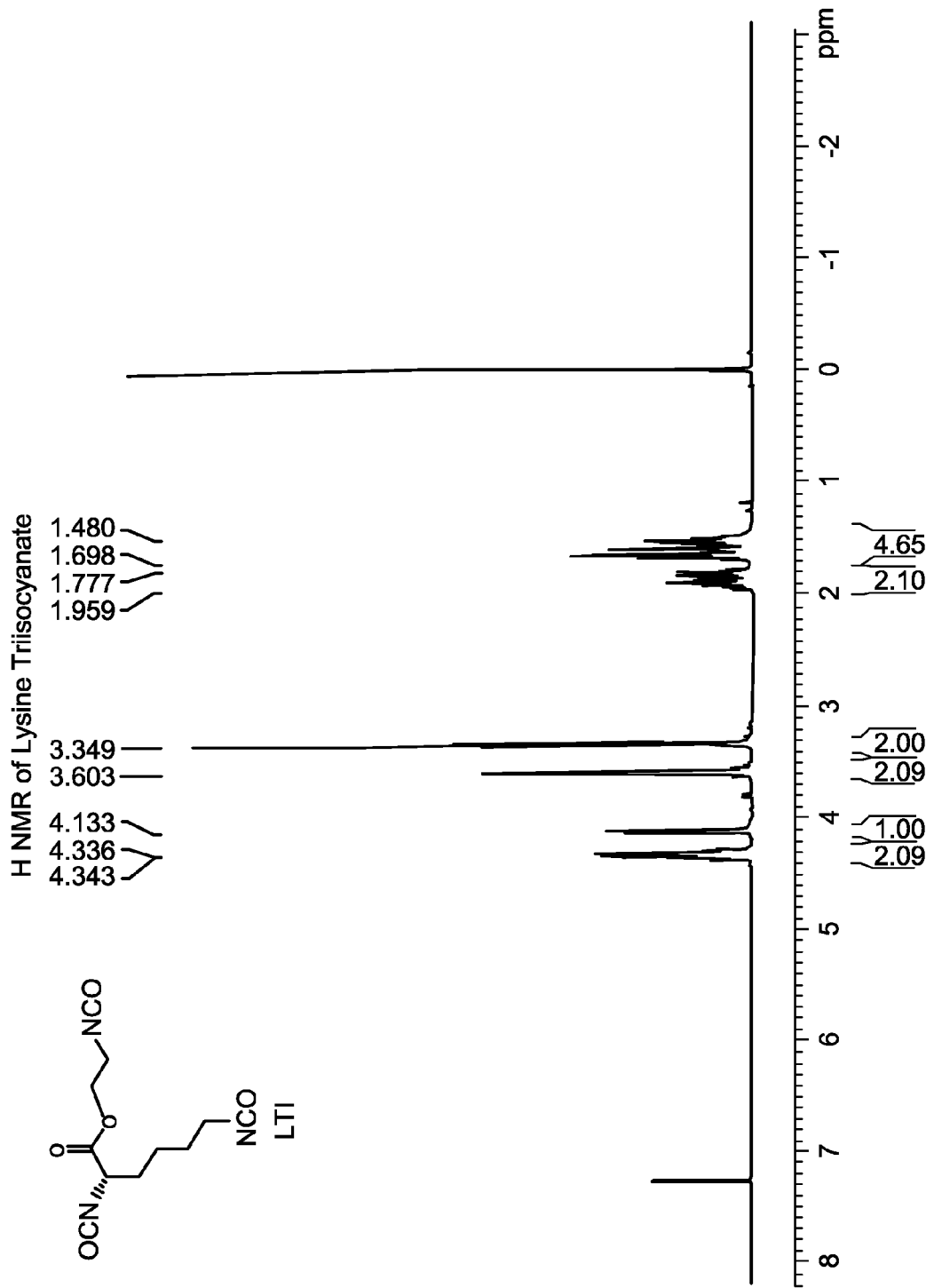
FIG. 2 is a graphic illustration of the $^1$H NMR data obtained from isolated and purified lysine ester triisocyanate.
Figure 3:
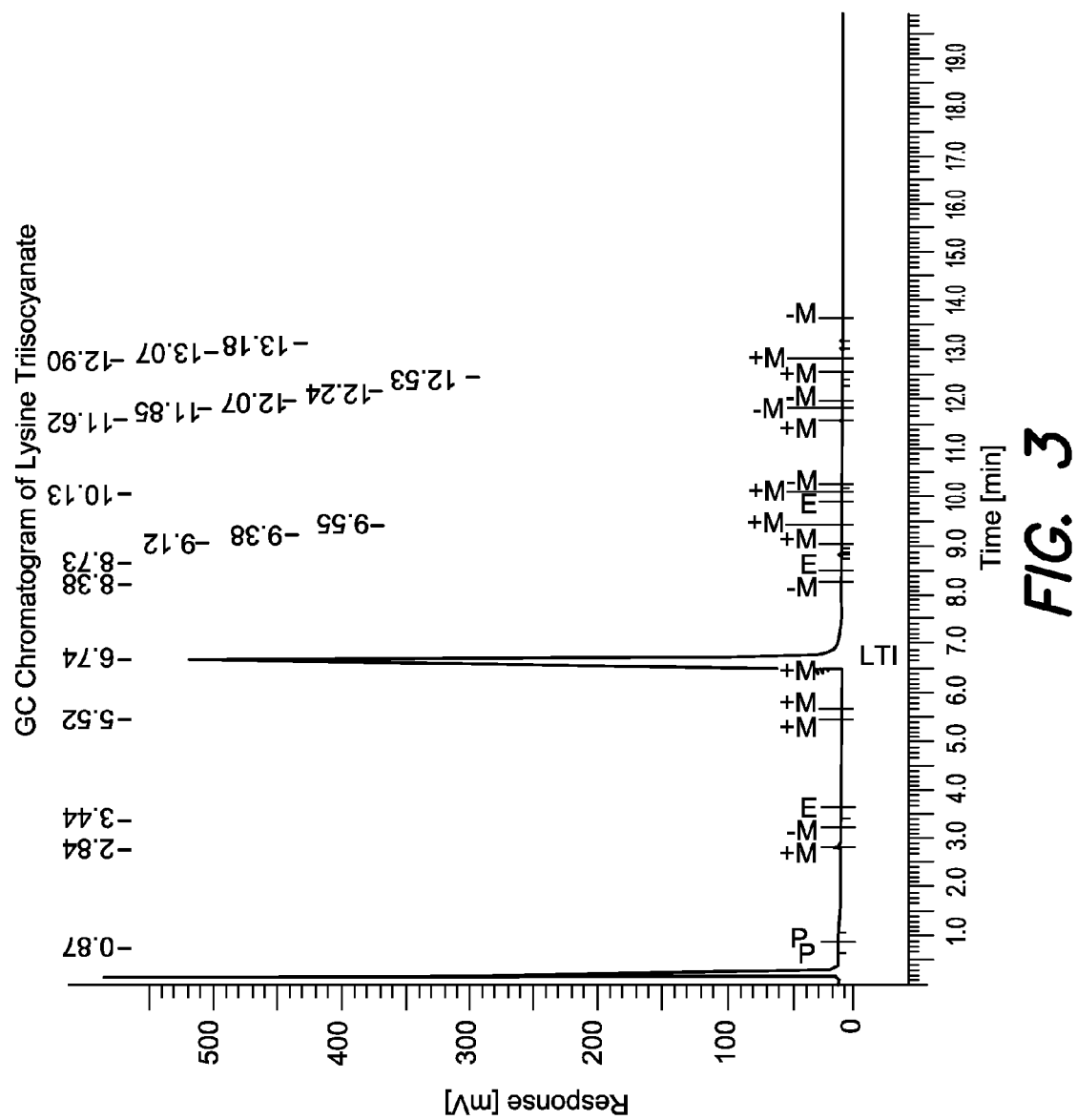
FIG. 3 is a graphic illustration of the gas chromatography data obtained from lysine ester triisocyanate.
Figure 4:
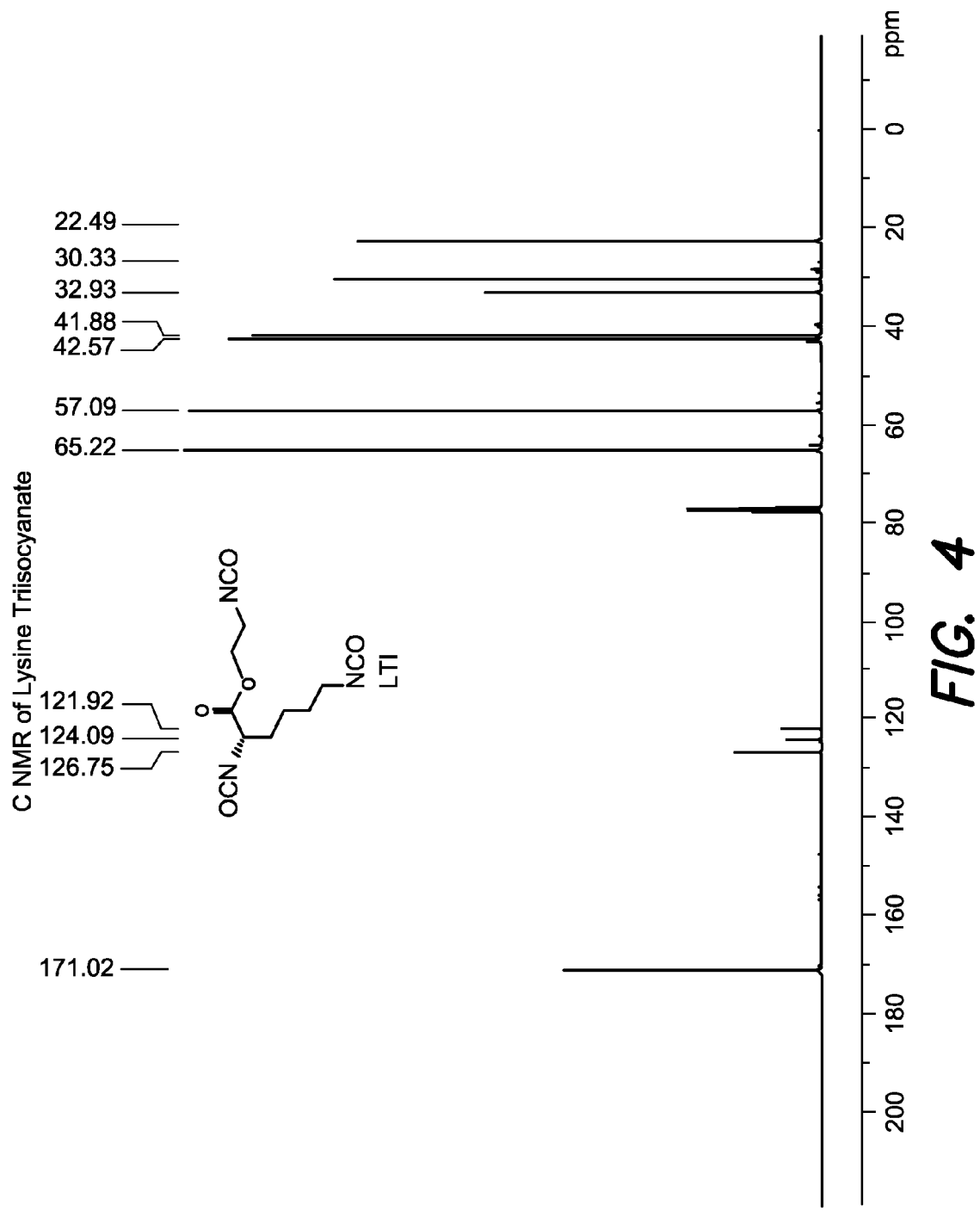
FIG. 4 is a graphic illustration of the $^{13}$C data obtained from lysine ester triisocyanate.

The product recovered from this reaction was combined with two other aliquots, giving a total of 1240 grams of oil. The oil was dissolved in 4 liters of MTBE and treated with 70 grams of activated carbon. The suspension was filtered and the solution concentrated to on rotary evaporator at 40° C. and 0.5 mm Hg for several hours. The product was recovered as an orange oil. Mass recovery was 1040 grams (84%, for purification). The purity was 98.0% by GC analysis. FIG. 2 is a graphic illustration of the $^1$H NMR data obtained from isolated and purified lysine ester triisocyanate. The lysine ester triisocyanate had high purity (e.g., at least 98%). FIG. 3 is a graphic illustration of the gas chromatography data obtained from lysine ester triisocyanate (e.g., at least 98% purity). FIG. 4 is a graphic illustration of the $^{13}$C data obtained from lysine ester triisocyanate. The lysine ester triisocyanate had high purity (e.g., at least than 98%).

Results and Discussion of Examples 2 and 3

The solvent used in previous preparations of lysine ester triisocyanate (LTI) was dichlorobenzene. The boiling point of dichlorobenzene was sufficiently high that it interfered with the purification of LTI. Two separate wiped-film still distillations were required to remove dichlorobenzene and subsequently purify LTI. Substituting chlorobenzene as solvent was shown to be equally effective and residual solvent levels could be reduced to acceptable levels by heating under high vacuum without distillation. Many attempts were made to use triphosgene directly with the trihydrochloride salt. These included addition at high temperature and use of activated carbon to decompose triphosgene into phosgene, in situ. No significant product formation was observed. Use of triphosgene in the presence of pyridine appeared promising, initially. However, it was determined that all the reaction was occurring during the work-up procedure. It was postulated that pyridine and phosgene form a complex which is unreactive. During work-up, the complex is decomposed and whatever residual phosgene is present reacts to give small amounts of LTI.

The most effective method was found to be the use of phosgene by direct addition as a gas or, more safely and effectively, as a solution in chlorobenzene (shown in Scheme 3). There were several factors identified for optimum reaction. These include that the phosgene solution could be added slowly so as not to build up a large inventory of phosgene. High levels of phosgene present in the reaction mixture reduced the reflux temperature and this slowed the reaction rate significantly. The highest reaction rate was observed at or above 120° C. Addition of phosgene as a solution was safer since any exothermic reaction could be controlled by slowing or stopping addition of the reagent. Phosgene solution could be added until nearly all the solids had disappeared, which implied reaction completion. This would result in a minimum use of phosgene, leaving less phosgene to be removed and quenched. Scheme 3 shows a method of making phosgene that can be used in the synthesis process. Apart from the danger associated with phosgene gas, its use at lab scale presents several issues which must be overcome. Small cylinders of phosgene are expensive, difficult to procure and are limited to one or few suppliers. For our purposes, the phosgene used was prepared on-site by thermal and catalytic decomposition of triphosgene directly into phosgene ("phosgene generator"), Scheme 4. The gas which evolved from the phosgene generator was trapped by formation of a solution in chlorobenzene. Very high concentrations of phosgene in chlorobenzene could be achieved (greater than 50 wt % is possible). In general, the concentration of phosgene was limited to 25 to 30 wt %. The initial catalyst chosen for the phosgene preparation was cobalt phthalocyanine. There were reports that indicated that this catalyst gave the fastest and most efficient conversion of triphosgene to phosgene. At first, the catalyst proved effective, but later scaled-up reactions stalled after a slow initiation and would only generate phosgene very slowly. Increasing the reaction temperature helped somewhat, but only thermal decomposition may have been observed. Use of 1,10-phenanthroline as catalyst proved to be much more reliable and repeatable. 1,10-phenanthroline could even be added to a stalled cobalt phthalocyanine-catalyzed reaction and force the reaction to completion. Using this method, almost 2 kilograms of phosgene was prepared in the lab, as a solution in chlorobenzene. NMR proved to be an effective way to monitor reaction progress by looking for the disappearance of starting trihydrochloride salt.

Isolation of Lysine Ester Triisocyanate

In the previous campaign for the preparation of LTI, the final product was isolated by triple distillation. The first distillation was for removal of residual dichlorobenzene. The second distillation was for removal of an impurity (diisocyanate-methyl ester.) The final distillation was to isolate pure LTI. It was observed that the recrystallization of the intermediate trihydrochloride salt developed in this campaign gave very low levels of the methyl ester impurity. Also, substitution of dichlorobenzene with chlorobenzene allowed for easy removal by high vacuum and heating. This avoided two of the previous distillations. 1H NMR analysis indicated that the LTI product was of high purity. A simple treatment of the isolated oil by treatment with activated carbon (to decolorize) in MTBE solution resulted in a product of acceptable appearance and purity. Polymeric by-product impurities were found to be insoluble in MTBE and were easily removed during filtration of the carbon. In this manner, distillation of the final product was eliminated from the process.

Example 4

LTI-PEG Preparation

LTI (250 grams, 0.94 moles) was charged to a flask fitted with a mechanical stirrer and thermocouple. The flask was heated to 80° C. in an oil bath. PEG-200 (93.9 grams, 0.47 moles) was added to the stirred mixture over 1.5 hours using a metering pump. After the addition was complete, the mixture was stirred for an additional 2 hours at temperature. The resulting viscous oil was decanted to a storage bottle, purged with nitrogen and stored at −20° C. Mass recovery was 320 grams. The yield loss was a result of the difficulty of completely transferring the viscous material out of the reaction flask.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of making phosgene, the method comprising heating triphosgene to form phosgene gas and contacting the phosgene gas with chlorobenzene or dichlorobenzene liquid to recover the phosgene gas in the liquid.

2. A method of making phosgene according to claim 1, wherein the triphosgene is heated in the presence of a catalyst and recovered in chlorobenzene.

3. A method of making phosgene according to claim 2, wherein (i) the catalyst comprises phenanthroline or (ii) the triphosgene is heated to a temperature from about 100° C. to about 200° C.

4. A method of making phosgene according to claim 3, wherein the catalyst comprises 1,10 phenanthroline.

* * * * *